(12) United States Patent
Frey

(10) Patent No.: US 6,468,427 B1
(45) Date of Patent: Oct. 22, 2002

(54) FLUID FILTER FOR USE IN EXTRACORPOREAL BLOOD PROCESSING

(75) Inventor: Helmut Frey, Williamsburg, VA (US)

(73) Assignee: Gambro, Inc., Lakewood, CO (US)

( * ) Notice: Subject to any disclaimer, the term of this patent is extended or adjusted under 35 U.S.C. 154(b) by 0 days.

(21) Appl. No.: 09/400,211

(22) Filed: Sep. 21, 1999

Related U.S. Application Data

(60) Provisional application No. 60/102,252, filed on Sep. 29, 1998.

(51) Int. Cl.$^7$ .......................... B01D 29/33; B01D 39/16
(52) U.S. Cl. ............... 210/497.01; 210/498; 210/497.3; 210/304; 210/448; 210/500.27
(58) Field of Search ............................ 210/497.01, 498, 210/323.2, 443–444, 452, 483, 496, 456, 645, 644, 457, 448, 320, 304, 512, 500.27, 497.3; 55/525; 264/512–513, 563; 604/6.01, 6.09, 90, 6.15, 6.16, 7, 252; 422/42, 44–45, 101

(56) References Cited

U.S. PATENT DOCUMENTS

| | | | |
|---|---|---|---|
| 2,595,923 A | * | 5/1952 | Carlson |
| 2,704,544 A | * | 3/1955 | Ryan |
| 3,492,991 A | * | 2/1970 | Dyer, Jr. |
| 4,052,315 A | * | 10/1977 | Lindsay, Jr. et al. ........ 210/232 |
| 4,233,159 A | * | 11/1980 | Senda et al. ................. 210/143 |
| 4,406,326 A | * | 9/1983 | Wagner |
| 4,427,547 A | * | 1/1984 | Miller et al. ................. 210/411 |
| 4,666,598 A | * | 5/1987 | Heath et al. ................. 210/239 |
| 4,770,787 A | | 9/1988 | Heath et al. |
| 4,882,055 A | * | 11/1989 | Stamstad .................... 210/483 |
| 5,024,771 A | * | 6/1991 | Chiarito |
| 5,330,425 A | * | 7/1994 | Utterberg |
| 5,489,385 A | * | 2/1996 | Raabe et al. |
| 5,503,801 A | | 4/1996 | Brugger |
| 5,545,318 A | | 8/1996 | Richmand et al. |
| 5,591,251 A | | 1/1997 | Brugger |

FOREIGN PATENT DOCUMENTS

| | | | |
|---|---|---|---|
| EP | 0614675 B1 | | 10/1997 |
| GB | 579562 | | 8/1946 |
| WO | 96/26315 | * | 8/1996 |

OTHER PUBLICATIONS

Jacqueline I. Kroschwitz, *Blow Molding*, Concise Encyclopedia of Polymer Science and Engineering, pp. 90–92 (1990).

Jacqueline I. Kroschwitz, *Injection Molding*, Concise Encyclopedia of Polymer Science and Engineering, pp. 469–472 (1990).

* cited by examiner

Primary Examiner—Matthew O. Savage
Assistant Examiner—Marianne Ocampo
(74) Attorney, Agent, or Firm—Peter B. Scull; Edna M. O'Connor; Laura M. Butterfield

(57) ABSTRACT

A filter having a substantially cylindrical or slightly tapered body design which has a plurality of elongated apertures formed therethrough. Each aperture is defined side to side by a pair of elongated, wedge-like rib members disposed one on each side of each aperture, and top to bottom by a pair of cross members which present a substantially square top side and an angularly declining bottom side. The end effect is a substantially rectangular entry aperture for fluid flow with the exception of the declining bottom side which promotes smooth, low resistance entry flow. The present invention is also directed to a method of manufacture of filters having the above-described characteristics. In particular, the preferred method involves an injection molding process in which a molten plastic (such as high-density polyethylene, HDPE) is injected into a two-part mold. The mold generally comprises a smooth, substantially cylindrical cavity and a notched and grooved core which is inserted into the cavity in a partial surface to surface contact relationship to complete the filter mold. Due to the extremely close tolerances required by a such a core and cavity surface to surface relationship, unique mold alignment modifications were also developed.

21 Claims, 11 Drawing Sheets

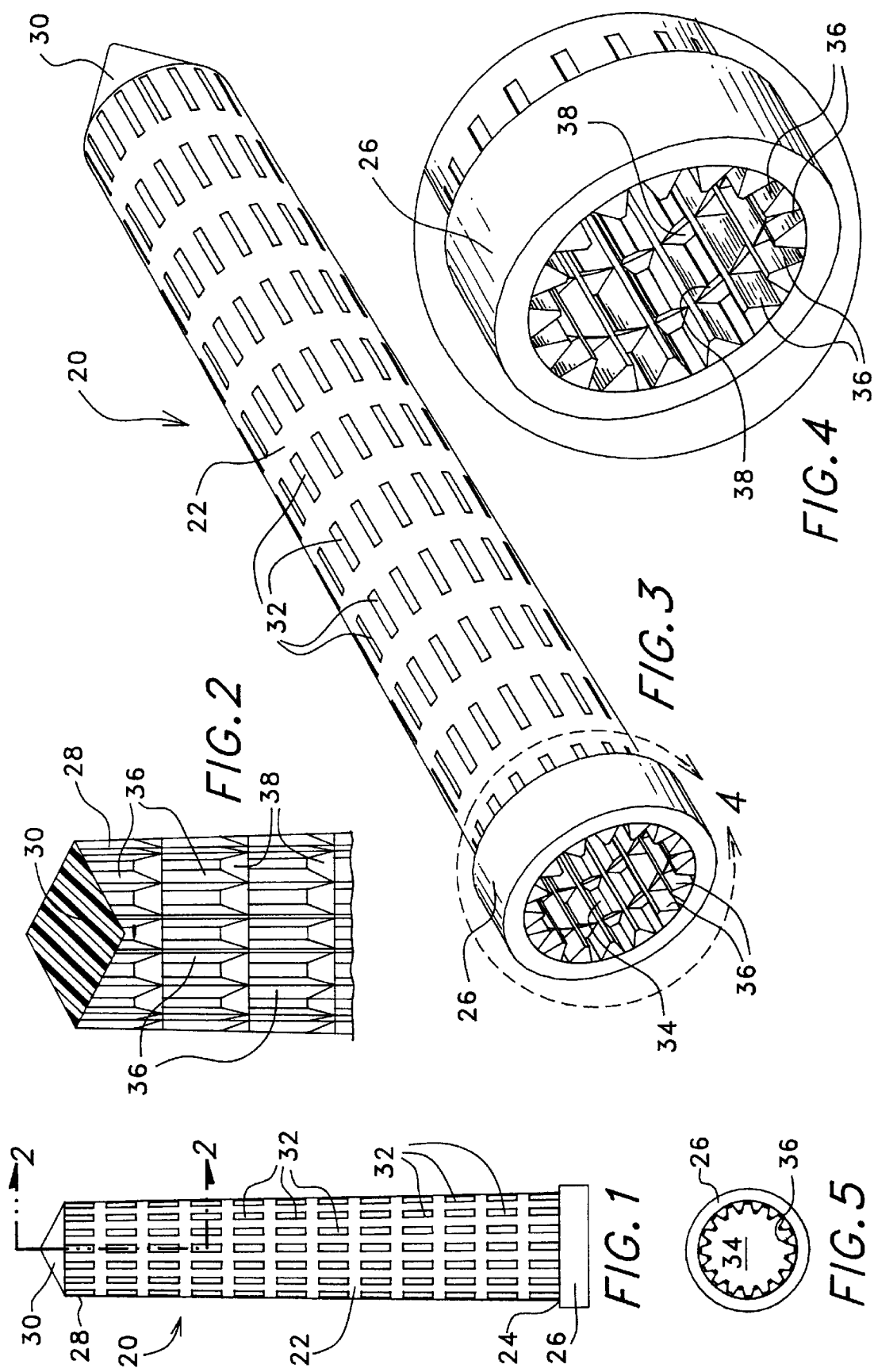

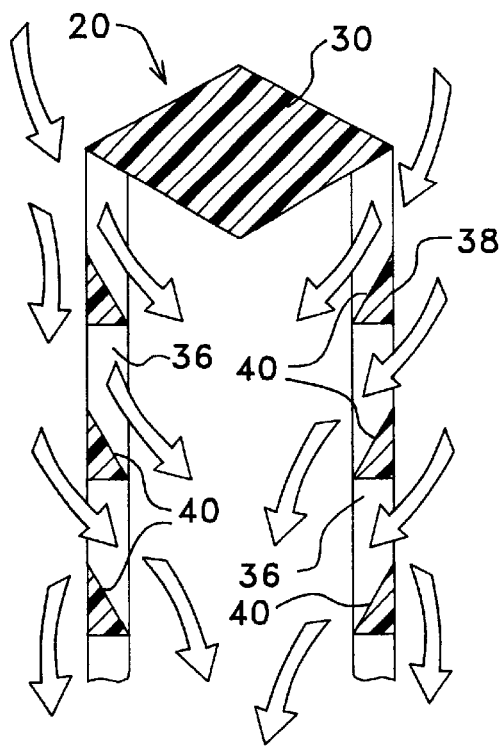
FIG. 7
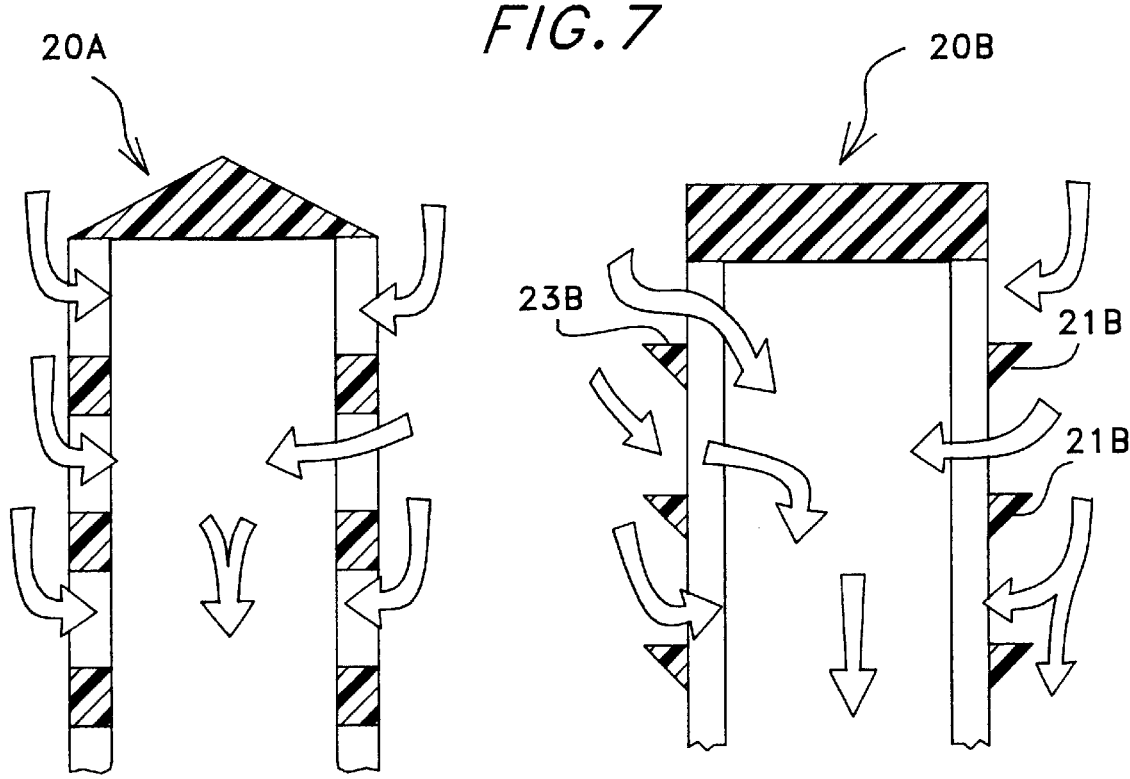
FIG. 8
(PRIOR ART)
FIG. 9
(PRIOR ART)

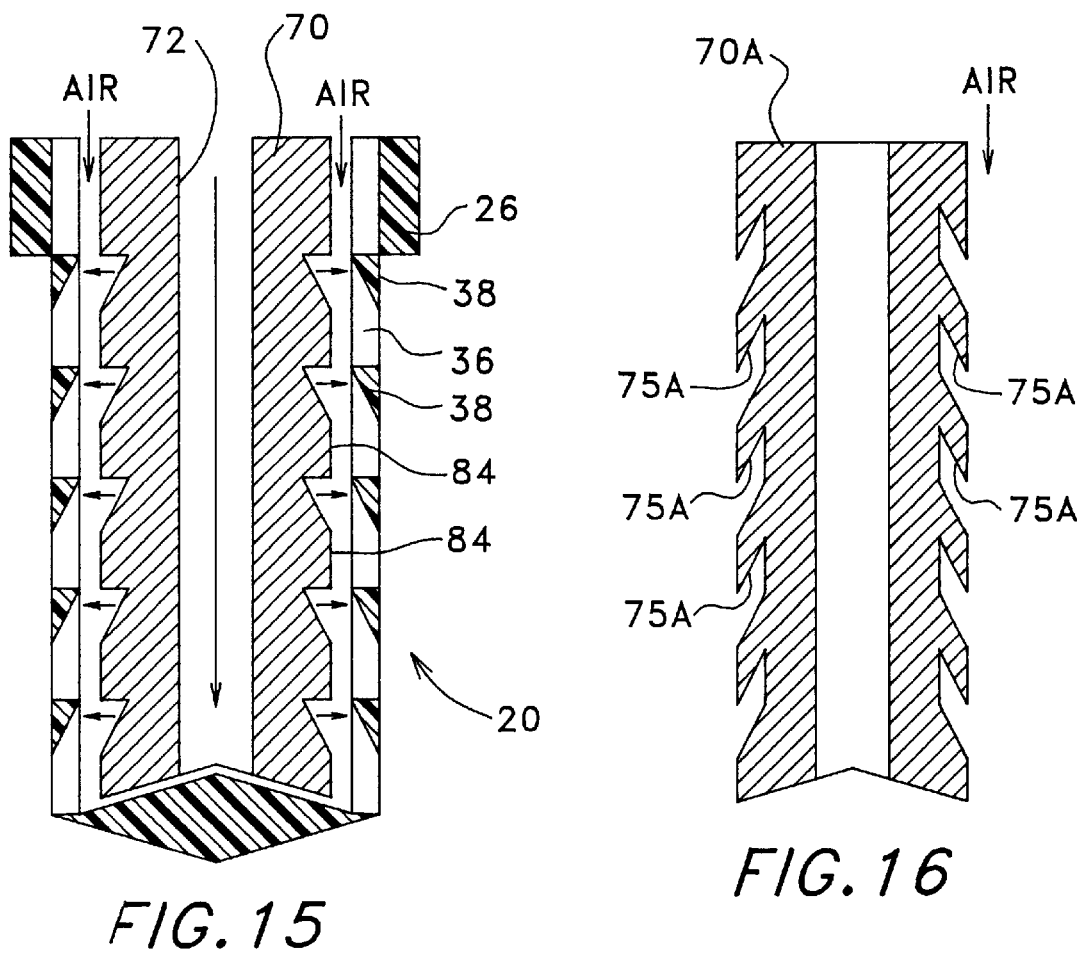
FIG. 15
FIG. 16
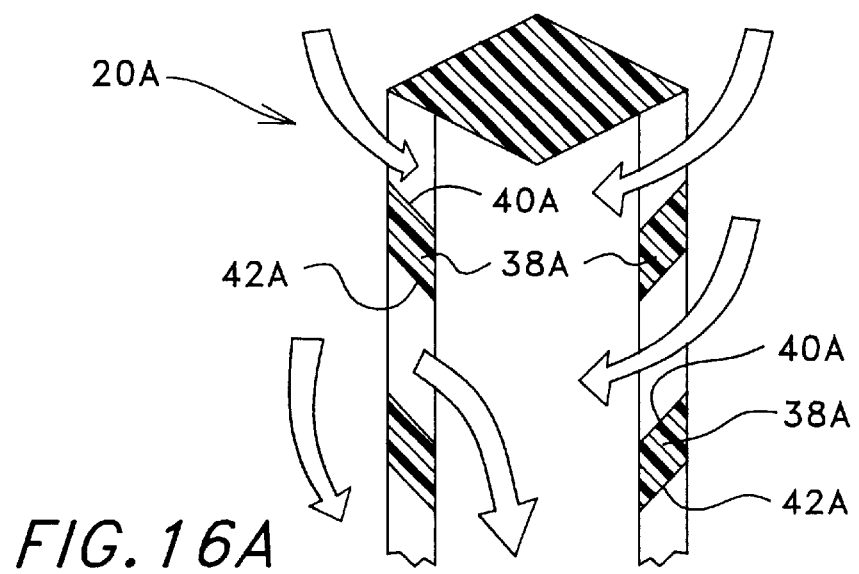
FIG. 16A

FLUID FILTER FOR USE IN EXTRACORPOREAL BLOOD PROCESSING

This application claims the benefit of U.S. Provisional Application No. 60/102,252 filed Sep. 29, 1998.

FIELD OF THE INVENTION

The present invention relates generally to fluid filters and more particularly to a filter which has distinctive inlet apertures defined, in part, by angularly declining surfaces. This invention further relates particularly to methods for making such filters. Filters of this invention present a distinct advantage in extracorporeal blood systems.

BACKGROUND OF THE INVENTION

Fluid filters come in many shapes and sizes depending primarily on their intended usage. For example, filters positioned at the inlet to a pipe or tubing system are often also tubular in form. Conical and tapered cylindrical forms are alternatives used in these situations as well. Aperture size and quantity may also drive the ultimate geometric shape chosen for use. So too may the fluid to be filtered.

An example of a fluid system having special requirements which can be significantly impacted by filter shape is a blood flow system outside the body, i.e., an extracorporeal blood system. Poor flow patterns can create problems for blood flowing through an extracorporeal blood system. Excessively turbulent or unduly slowed or stagnated blood flow may activate the blood's clotting processes causing the formation of blood clots and strands in the blood. Clotting of blood in an extracorporeal blood system may result in occlusion of the tubing lines or in injury to the patient.

Extracorporeal blood systems usually include devices commonly known as drip chambers or bubble traps (referred to herein generally as bubble traps). One purpose of such devices is to capture and remove potentially harmful elements (such as air bubbles or blood clots) from the blood prior to treating the blood or returning it to the patient. Filters are often used to assist in this removal, particularly for catching blood clots and other particulates. A typical filter of this type is a conical or cylindrical device having numerous perforations formed therein. Examples of such filters can be found used in the bubble traps disclosed in the U.S. Patents to Brugger (U.S. Pat. Nos. 5,503,801 and 5,591,251) and Raabe et al. (U.S. Pat. No. 5,489,385). A bubble trap with a filter of this type is also commonly incorporated into and thereby forms a distinct part of a cartridge cassette of an extracorporeal blood tubing and cartridge set such as those disclosed in the U.S. Patents to Heath et al. (U.S. Pat. Nos. 4,666,598 and 4,770,787), inter alia.

It is believed that numerous filter designs may promote blood clotting because, among other possible detriments, they present an inherent resistance to ordinary blood flow. Resistance in a blood flow path slows the blood's progress which, in turn, allows the blood to initiate clotting. Such clotting can occur at points of stagnation or along surfaces presenting a high degree of frictional resistance. Resistance may also cause turbulence in blood flow filters and is thus sought to be avoided here as well. Turbulent blood flow may lead to clotting or the formation of air bubbles in the blood. If returned to the patient in the blood, either of these present a risk of adverse health consequences to the patient.

Though still operable for passing blood, filters of the prior art nevertheless suffer geometric inefficiencies which present friction, stagnation and/or general slowing of the blood flow; any of which conditions possibly leading to blood clotting. For instance, the filters in the bubble traps of Brugger '801 and '251 (referred to above) present a plurality of substantially square, right-angled entry windows (in cross-section) which force the generally downwardly flowing blood in those bubble traps to make right-angled turns in order to enter the respective filters. Such right-angled turns can have the effect of slowing the blood flow as well as creating stagnation points at the lines of flow divergence. The filter designs of Raabe et al. '385 suffer similar geometrical, flow-impairing drawbacks. The filters shown in Raabe have external projections which also force substantially right angled flow redirections for entry of blood into those filters. It is thought that such redirections cause slowing and stagnation which may promote clotting and thereby, flow restrictions.

Thus, it is apparent that there remains a distinct need for continued improvements in blood flow filters which effectively remove solids from the blood yet provide unhindered passage of the blood therethrough. It is toward this end that the present invention is directed.

SUMMARY OF THE INVENTION

The filter of the present invention has a substantially cylindrical or slightly tapered body design which has a plurality of elongated apertures formed therethrough. Each aperture is defined side to side by a pair of elongated, wedge-like rib members disposed one on each side of each aperture, and top to bottom by a pair of cross members which present a substantially square top side and an angularly declining bottom side. The end effect is a substantially rectangular entry aperture for fluid flow with the exception of the declining bottom side which promotes smooth, low resistance entry flow.

The present invention is also directed to a method of manufacture of filters having the above-described characteristics. In particular, the preferred method involves an injection molding process in which a molten plastic (such as high-density polyethylene, HDPE) is injected into a two-part mold. The mold generally comprises a smooth, substantially cylindrical cavity and a notched and grooved core which is inserted into the cavity in a partial surface to surface sealing contact relationship to complete the filter mold. Due to the extremely close tolerances required by a such a core and cavity surface to surface sealing relationship, unique mold alignment modifications were also developed.

These and other features of the present invention will be further illuminated in the following detailed description read in conjunction with the accompanying drawings which are described briefly below.

BRIEF DESCRIPTION OF THE DRAWINGS

FIG. 1 is a side elevation of a filter of the present invention;

FIG. 2 is a cross-sectional view of a portion of the filter of FIG. 1 taken from the circled area 2 thereof;

FIG. 3 is an isometric view of the filter of FIG. 1;

FIG. 4 is an enlarged view of the portion inside circled area 4 of FIG. 3;

FIG. 5 is a bottom plan view of the filter of FIG. 1;

FIG. 7 is a generalized illustration related to the filter of FIGS. 1–6 showing fluid flow therethrough;

FIG. 8 is a generalized illustration showing fluid flow through a filter of the prior art;

FIG. 9 is another generalized illustration showing fluid flow through yet another filter of the prior art;

FIG. 15 is an exaggerated, schematic view of a core and filter illustrating the ejection technique used to remove the filter from the core;

FIG. 16 is a schematic view of an alternatively shaped core for an ejection technique comparison relative to FIG. 15;

FIG. 16A is a generalized flow diagram for the filter resulting from the alternatively shaped core of FIG. 16;

DETAILED DESCRIPTION

Figure 6:
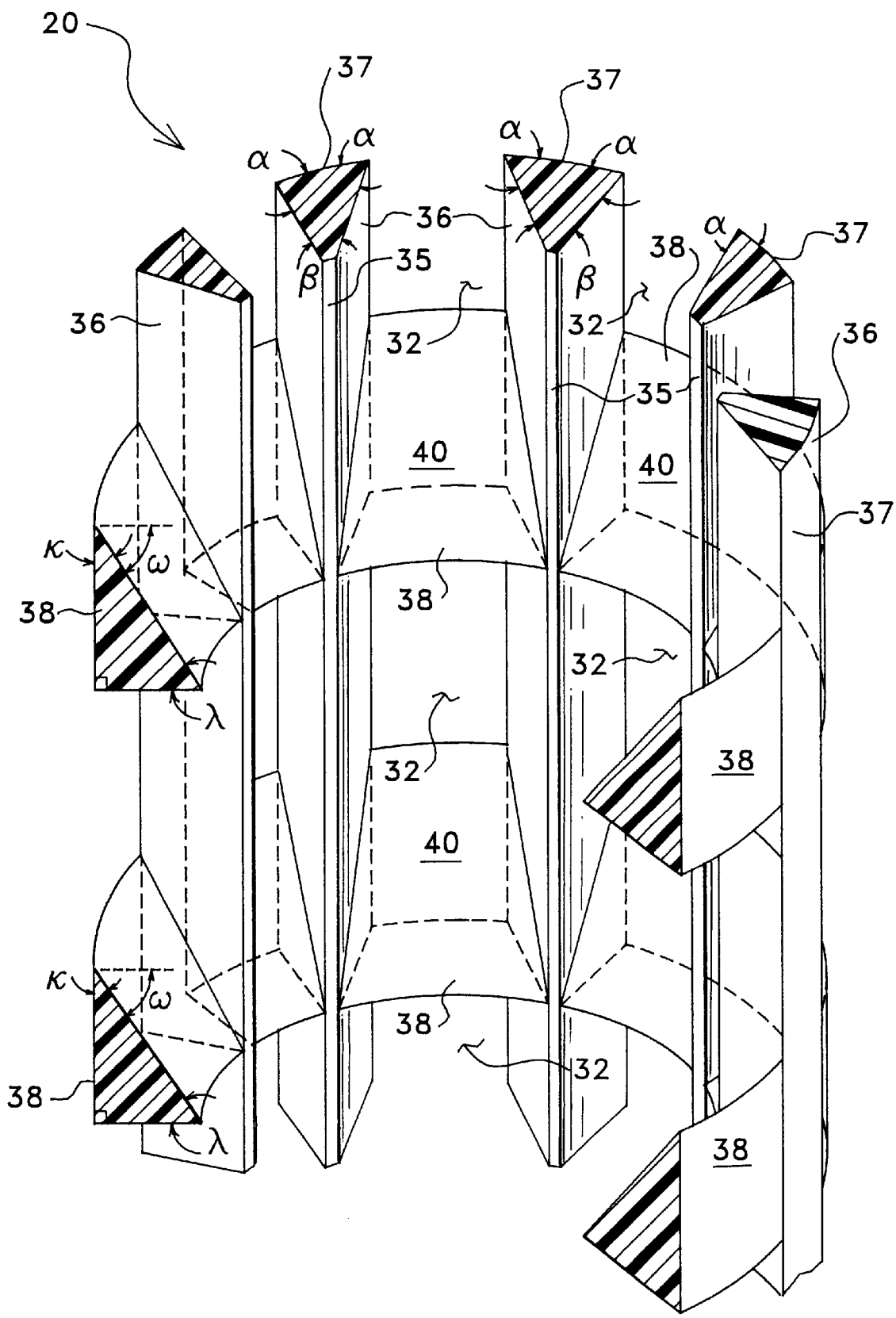
FIG. 6 is an enlarged, isometric, substantially two-thirds view of the interior of the filter of FIG. 1 taken from the circled area 6 thereof.

The present invention is directed to a filter which is shown in the attached drawings and identified generally by the reference numeral 20. In particular and as shown primarily in FIGS. 1 and 3, filter 20 comprises a hollow, substantially cylindrical or tubular body portion 22 which has at its open lower end 24 a flange 26 and at its closed upper end 28 a header 30. The exterior surface of the tubular body portion is substantially smooth. Defined in and through body portion 22 are a plurality of apertures 32 through which the fluid to be filtered passes when filter 20 is in use. Note, while in use, fluid is intended to flow from the exterior of filter 20 to its interior open area identified generally by the reference numeral 34 in FIGS. 3 and 5, for example.

As shown in more detail in FIGS. 2–4, apertures 32 are defined by longitudinally extending rib members 36 and by declining, fillet-type cross portions 38. As viewed in FIGS. 2–4, the rib members 36 and the cross portions 38 may appear to be separate entities, however, they are instead integrally formed during the injection molding process to be described below. The exterior view of filter 20 shown in FIGS. 1 and 3 better shows the integrality of rib members 36 and cross portions 38.

As can be seen from FIGS. 3–5, but still more particularly in FIG. 6, the elongated rib members 36 are substantially prismatic wedge-shaped members each having a relatively narrower nose portion 35 and a relatively wider base 37. The respective nose portions 35 of each of the wedges are faced inwardly toward the open interior 34 of the filter 20. Rib members 36 preferably have substantially isosceles triangularly shaped cross sections with convexly-rounded bases 37 corresponding to the external curvature of body 22. The two base angles α (alpha) of the isosceles triangles are substantially equal to each other as well as being substantially equal for all ribs 36. Similarly, the respective nose angles β (beta) are substantially equal to each other. Note, the sizes of the nose angles β are related to the sizes and quantities of apertures 32 desired for use in a filter 20. Angles β of between about 60 and about 90 degrees have been found practical although both smaller and larger angles will also be effective. Angles β of between about 80 and 85 degrees are currently preferred. Each of the nose portions 35 may, as shown, also be convexly-rounded, or alternatively concavely-rounded depending primarily on the method of manufacture (as this is described in more detail below). Also as shown in FIGS. 3–5, but more particularly in FIG. 6, the declining cross portions 38 are also substantially prismatic, here having substantially right triangularly shaped cross sections. Respective interior angles κ (kappa) and γ (lambda) are shown in FIG. 6 for the right triangular, cross sectional views of two exemplary cross portions 38. The angles κ of all the cross portions 38 are preferably 20 degrees, although other angles will also be effective. Note, an angle κ of 20 degrees corresponds generally to a preferred angle ω (omega) of about 70 degrees down from the horizontal. Angle ω thus defines the preferred angle of declination of faces 40 from the horizontal.

Cross portions 38 provide significance for filter 20 through their declining faces 40 as shown best in FIG. 6. These faces 40 furnish the distinct advantage of low resistance to the flow of the fluid as it enters filter 20. As shown by the flow arrows in FIG. 7, fluid enters the apertures 32 of filter 20 at an ever downward, albeit angular, orientation. In comparison, as shown by FIGS. 8 and 9, filters of the prior art present a substantially horizontal redirection of the entry flows therein. Note, filter 20A of FIG. 8 substantially represents the filters shown and described in the Brugger patents '801 and '251, and filter 20B of FIG. 9 substantially represents the cylindrical filters of Raabe '385. Raabe does have declining faces 21B on the undersides of the external cross portions 23B thereof; however, due to the injection molding process thereof which specifically involves external shaping (as described below), a forced horizontal inlet flow is inescapable.

Figure 10:
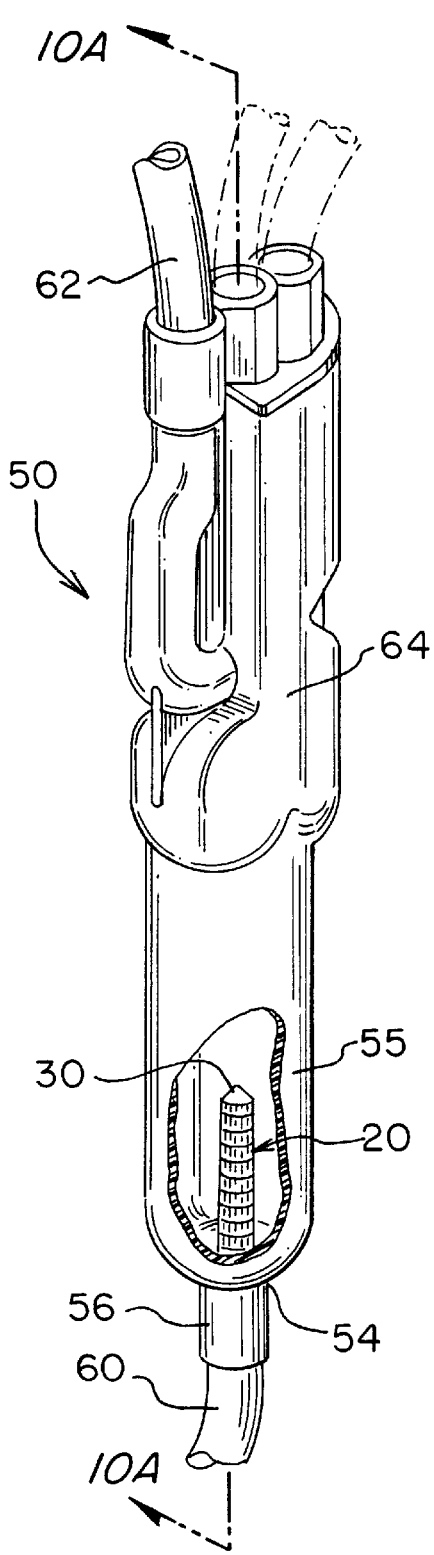
FIG. 10 is a perspective view of the filter of the present invention shown disposed for use inside a partially broken-away extracorporeal blood bubble trap chamber.
Figure 10A:
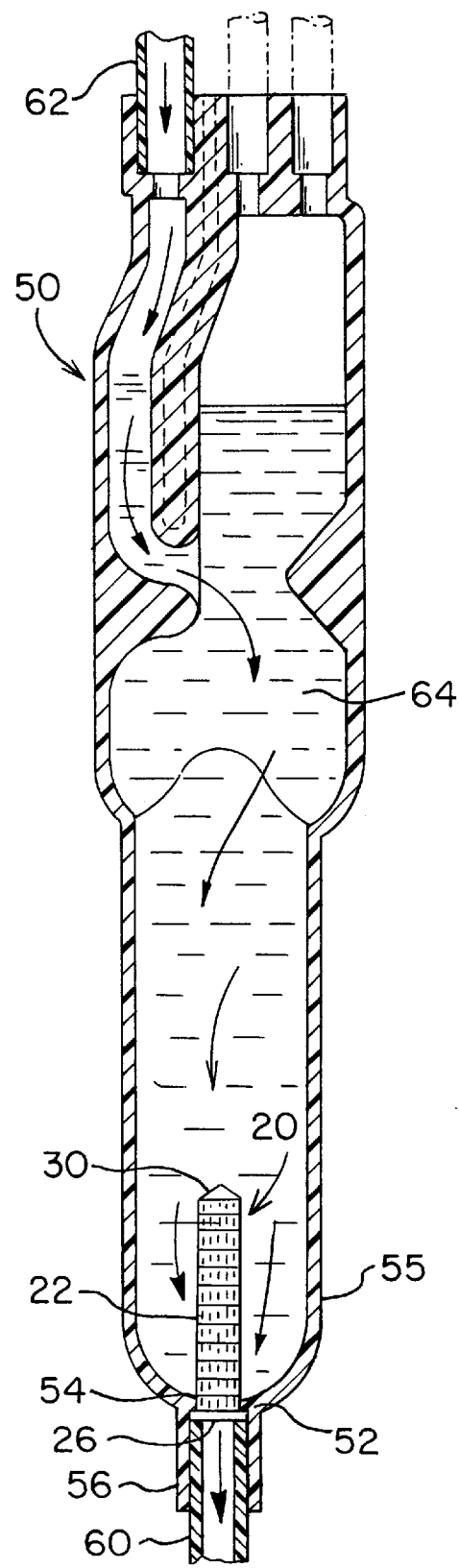
FIG. 10A is a cross-sectional view of the filter and bubble trap chamber of FIG. 10 taken along line A—A thereof showing the flow of fluid therethrough.

Before examining the respective manufacturing processes in detail, please refer to FIGS. 10 and 10A, in which a filter 20 of the present invention is shown in an exemplary use inside a blood circulating bubble trap chamber 50. Note that flange 26 is used to secure filter 20 in place within chamber 50. To do so, flange 26 will have a diameter wider than the diameter of the collar 52 of the chamber outlet/exit port 54. Thus, filter 20 is inserted in the outlet 54 and is disposed such that the body 22 and header 30 are fully, or substantially fully, positioned within the lower portion 55 of chamber 50. Flange 26 of filter 20 remains outside chamber 50 since it is wider than collar 52. An exit coupling 56 surrounds the exit port 54 and receives the flange 26 of filter 20 and also receivably retains exit conduit 60. The exit conduit 60 is frictionally engaged by and preferably solvent bonded to the exit coupling 56 with the filter flange 26 sandwiched between the exit conduit 60 and collar 52 thereby preventing dislocation of filter 20 and exit conduit 60 during extracorporeal treatment.

In operation, blood flows into chamber 50 through an inlet conduit 62 to an upper portion 64 of chamber 50. The blood flows downwardly toward the chamber outlet 54. Here, the blood flows through filter 20, out the exit port 54 and into and through exit conduit 60 ultimately back to the patient (not shown).

Figure 11:
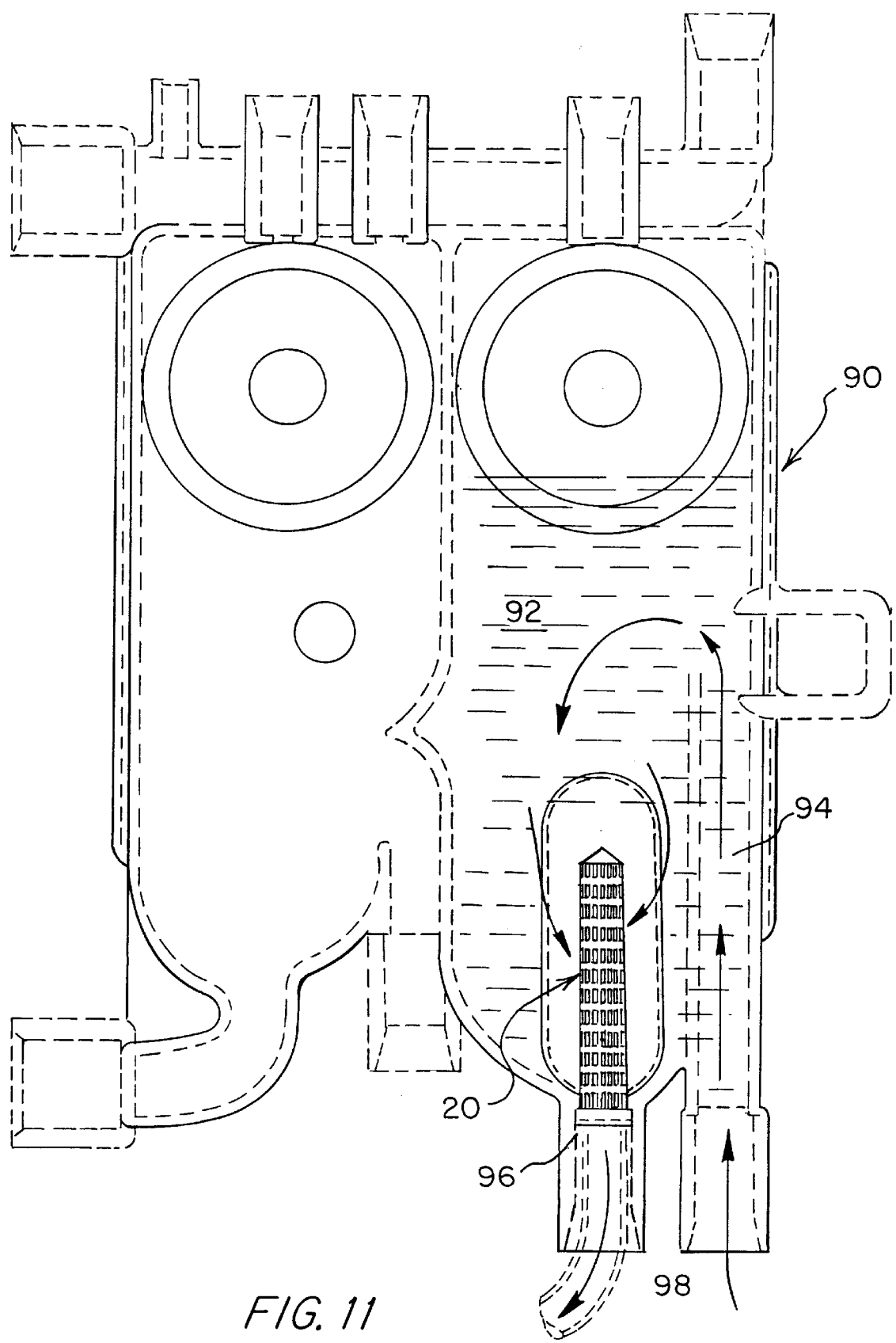
FIG. 11 is a side elevation of the filter of the present invention shown disposed for use inside a cartridge blood processing system.

Use with the bubble trap 50 of FIGS. 10 and 10A is, again, exemplary. Another exemplary use is inside a fluid flow cassette as disclosed in the U.S. patents to Heath et al. (U.S. Pat. Nos. 4,666,598 and 4,770,787), inter alia. The use of a filter 20 in such a device is shown schematically in FIG. 11. In much the same way blood entered the bubble trap 50 of FIGS. 10 and 10A, blood enters the filtering chamber 92 of cassette 90 through an inlet 94 (though from the bottom right in this example), and then flows through the chamber 92 downwardly to filter 20. The blood then enters the filter 20 and finally exits the cassette system through exit aperture 96. The blood then flows back to the patient (not shown) through an outlet conduit 98. The other portions of cassette 90 which are shown but not discussed are understood in the art as described in Heath et al. '598 and '787.

Also, entry aperture size and quantity is dictated somewhat by the pressure drop/head loss, and chamber outlet size as well as by the fluid to be filtered. It is thus, for example, preferred that the total inlet area of the totality of apertures 32 be greater than the outlet area(s) presented by either of the outlets 54 or 96 shown in FIGS. 10 and 11, respectively. Therefore, given an outlet area, then, the preferred number and sizes of apertures can be determined, with a ratio of size to total number giving some alternatives. Extracorporeal blood will also require a maximum aperture size. Thus, a maximum size per aperture will then dictate an overall number of apertures which, in turn, will dictate a minimum length and or width of a body 22. Similarly, aperture width in a filter of the above-described type, will also impact the wedge angle of the elongated ribs 36. Narrower aperture widths will usually require wider wedge angles (or more apertures circumferentially). Note, aperture sizes having 1.5 mm heights and from 0.20 to 0.35 mm widths have been found operable with less pressure drops than the prior art filters of Brugger and Heath et al. (502 mmHg average pressure drop of 10 prior art filters; compared to 433, 430, and 427 mmHg average pressure drops of 10 each of 0.20, 0.28 and 0.33 aperture width filters of the present invention).

Filter 20 is preferably constructed of substantially flexible HDPE (high-density polyethylene) using an injection molding manufacturing technique to be further described below. Flexibility allows for this particular part to be simply molded in that it allows for the core of the mold to be easily pulled from the finished filter even though there is some overlap of the filter on and within notches in the core. HDPE is also preferred because HDPE is biocompatable and both gas and gamma-sterilizable and is thus suitable for use in extracorporeal treatment systems through which blood will pass. Other materials are also foreseeably usable herewith. For example, polypropylene, polyvinyl chloride (PVC), linear low-density polyethylene (LLDP), or any polyolefin providing soft PVC rubber-like characteristics may be used in this invention.

Figure 12:
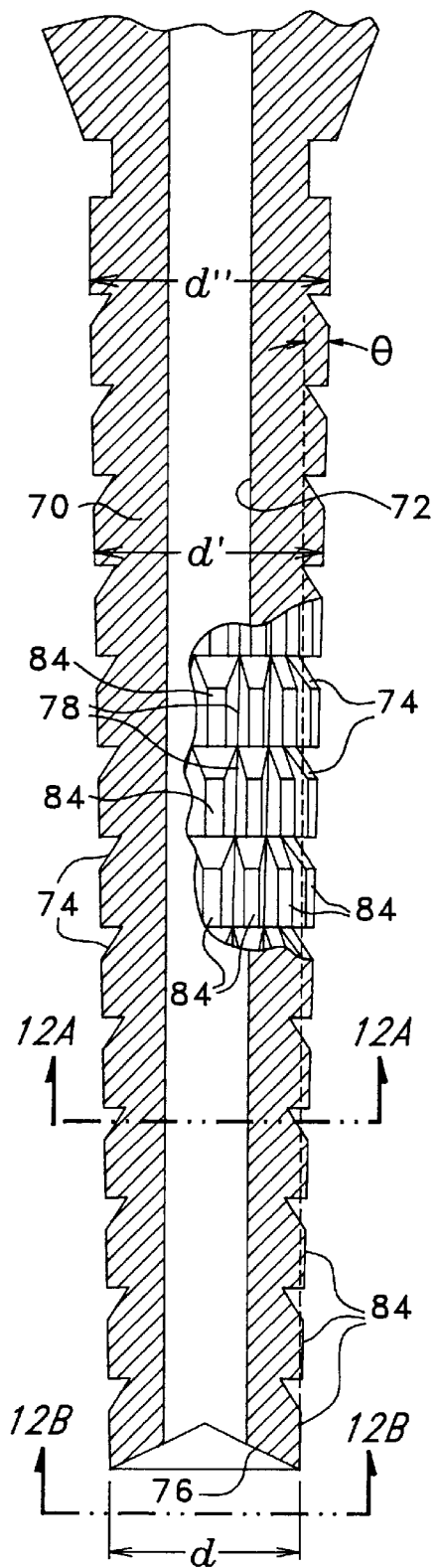
FIG. 12 is a broken, partially side elevational, mostly cross-sectional view of a core pin used during injection molding of the filter of the present invention.

In manufacturing a filter 20 of the present invention, the preferred method involves injection molding high-density polyethylene (HDPE) using primarily a two-part mold. The two parts include a smooth, substantially cylindrical cavity and a notched and grooved core. These mold elements are shown in more detail in FIGS. 12 and 13. As can be seen in FIG. 12, core 70, is a generally solid body having a hollowed cylindrical center portion 72 defined therein. Hollow portion 72 is used to house a knockout pin (not shown in FIG. 12). Core 70 also has a plurality of circumferential notches 74 defined therein which are used to form the angular, declining faces 40 of cross portions 38. A flat, hollowed conical area 76 is also shown in FIG. 12 at the lower end of core 70. Conical area 76 provides the opening used to create header 30 of filter 20.

Figure 12A:
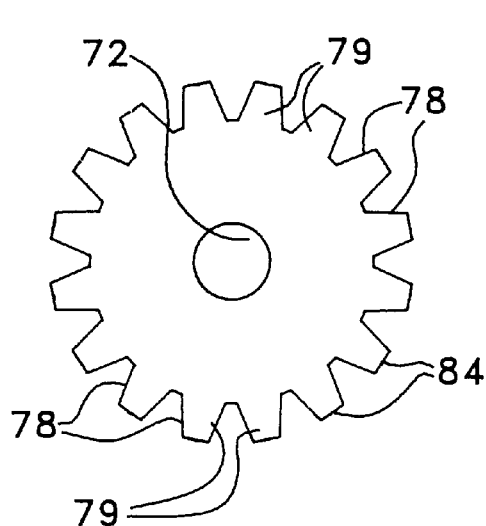
FIG. 12A is a bottom plan view of the core pin of FIG. 12 taken along line A—A thereof.
Figure 12B:
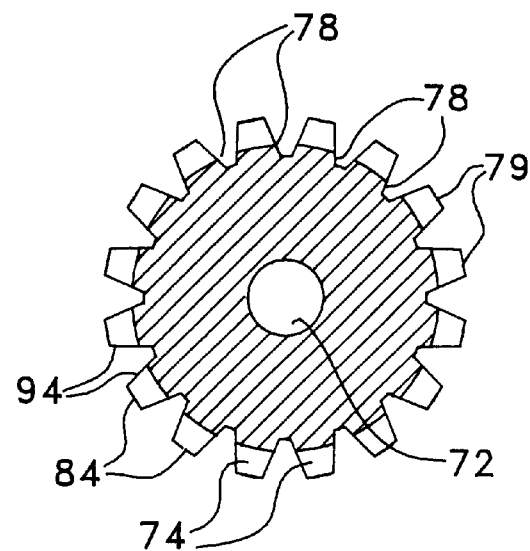
FIG. 12B is a cross-sectional view of the core pin of FIG. 12 taken along line B—B thereof.

FIGS. 12A and 12B help further illustrate the distinctive surface formations of core 70. In particular, FIG. 12A shows the end view of the elongated grooves 78 which are defined by and between elongated ridges 79. Grooves 78 form the mold voids which are used to cast the elongated, wedge-like ribs 36 running the length, top to bottom of the filter 20. Note, these ridges 78 are visible in FIG. 12 only in the side elevational portion thereof as the cross sectional portion of FIG. 12 is taken through the centers of diametrically opposed ridges 79, as shown by the cross-section defining lines 12—12 in FIGS. 12A and 12B. FIG. 12B shows a cross-section taken approximately mid notch to show the interconnection of notches 74 and grooves 78.

Figure 13:
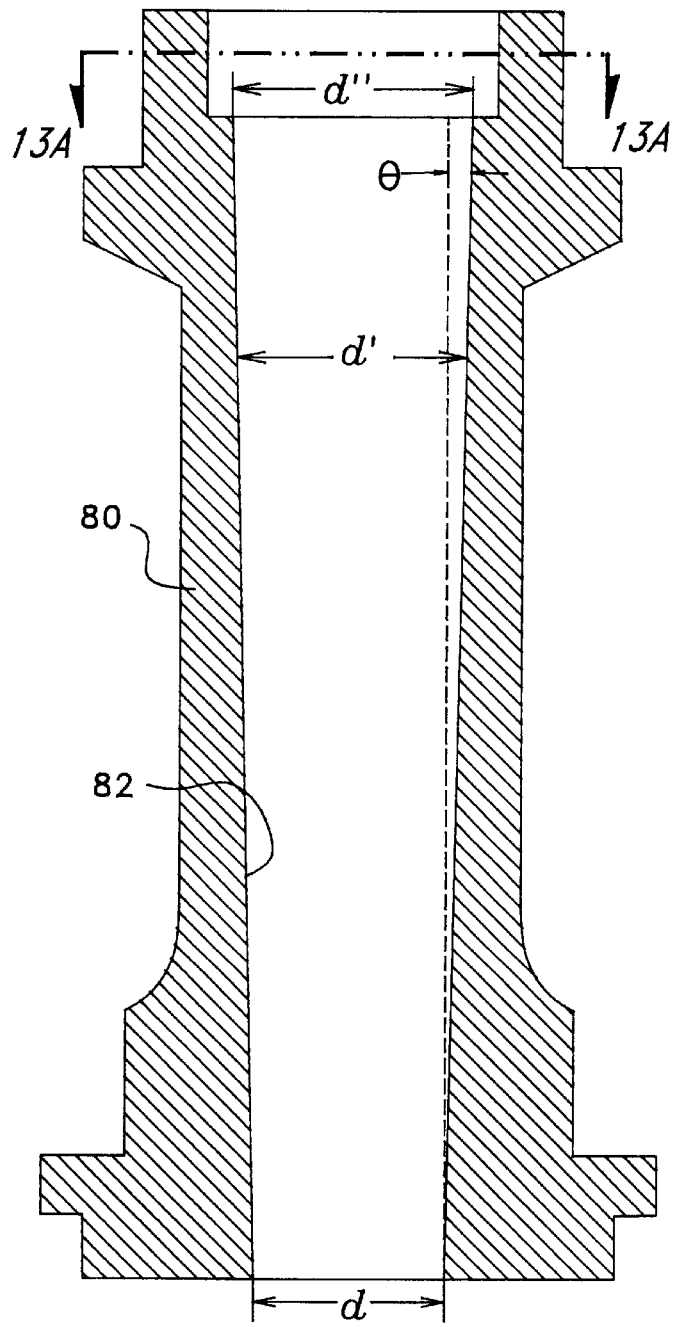
FIG. 13 is a cross-sectional view of a cavity into which the core pin of FIG. 13 is disposed during injection molding of a filter of the present invention.
Figure 13A:
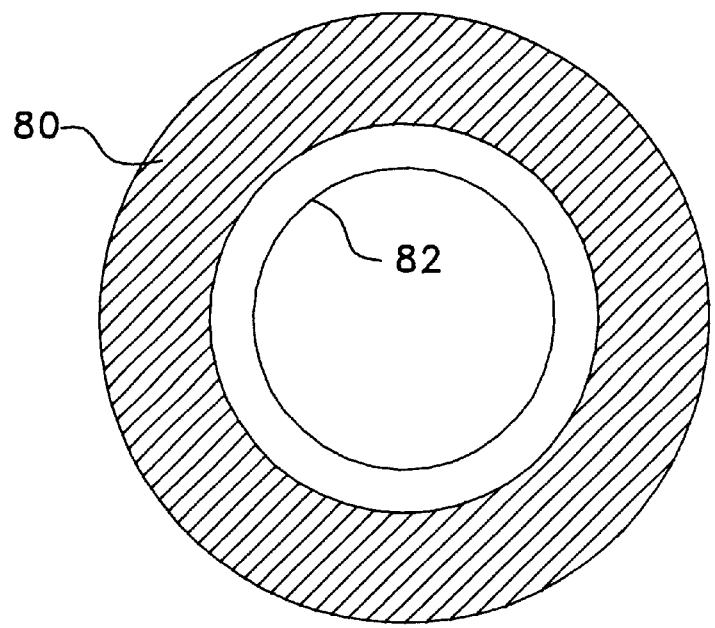
FIG. 13A is a cross-sectional view of the cavity of FIG. 13 taken along line A—A thereof.

FIGS. 13 and 13A show the cavity portion 80 of the mold of the present invention. Cavity 80 is a solid single member having a hollow substantially cylindrical opening 82 defined therethrough. Note, the preferred embodiment of filter 20 is substantially cylindrical yet slightly tapered as shown best by the angle $\Theta$ (theta) in FIG. 13. All depictions of the preferred embodiments herein are intended to have such an angle $\Theta$; for example, the core 70 of FIG. 12 is also formed with an inherent angle $\Theta$ as is also shown therein. Thus, a slightly tapered filter 20 will result. (Note, angle $\Theta$ is not shown relative to the filters of the previous FIGS. 1–11, though these filters also preferably have a taper defined by such an angle $\Theta$ as well.)

Furthermore, the core 70 of FIG. 12 will fit inside and meet sealingly wall to wall with the interior surface 82 of cavity 80. More specifically, each of the faces 84 at the apexes of ridges 79 of core 70 will meet wall to wall with interior surface 82. Sealingly means that each of these faces 84 contacts the interior surface 82 sufficiently so that the mold material will not be able to enter any space therebetween. Thus, sealingly here does not mean there are any elastic contacts; rather, only face to face contacts. These multiple surface contact areas thus define the ultimate apertures 32 formed in a finished filter 20. This therefore requires very precise machining of the corresponding mold tools; the core 70 and the corresponding cavity 80. Thus, the corresponding diameters at each contact point must be identical. More specifically, the angles $\Theta$ of core 70 and cavity 80 are identical. Likewise, diameter d of core 70, as shown at the lower end of the core in FIG. 12, is identical to corresponding diameter d of cavity 80 shown at the lower end of FIG. 13. Similarly, diameter d' at any height of core 70 must be identical to the d' at the corresponding height of cavity 80. Diameters d" at the corresponding top portions of core 70 and cavity 80 are thus also identical. This correspondence is shown in more detail in FIG. 14, where the core 70 is shown disposed inside the cavity 80. The interior surface 82 of cavity 80 is preferably diamond polished so that the exterior surfaces of resulting filters 20 will be as smooth as possible, thereby presenting still less resistance to fluid flow.

Figure 14:
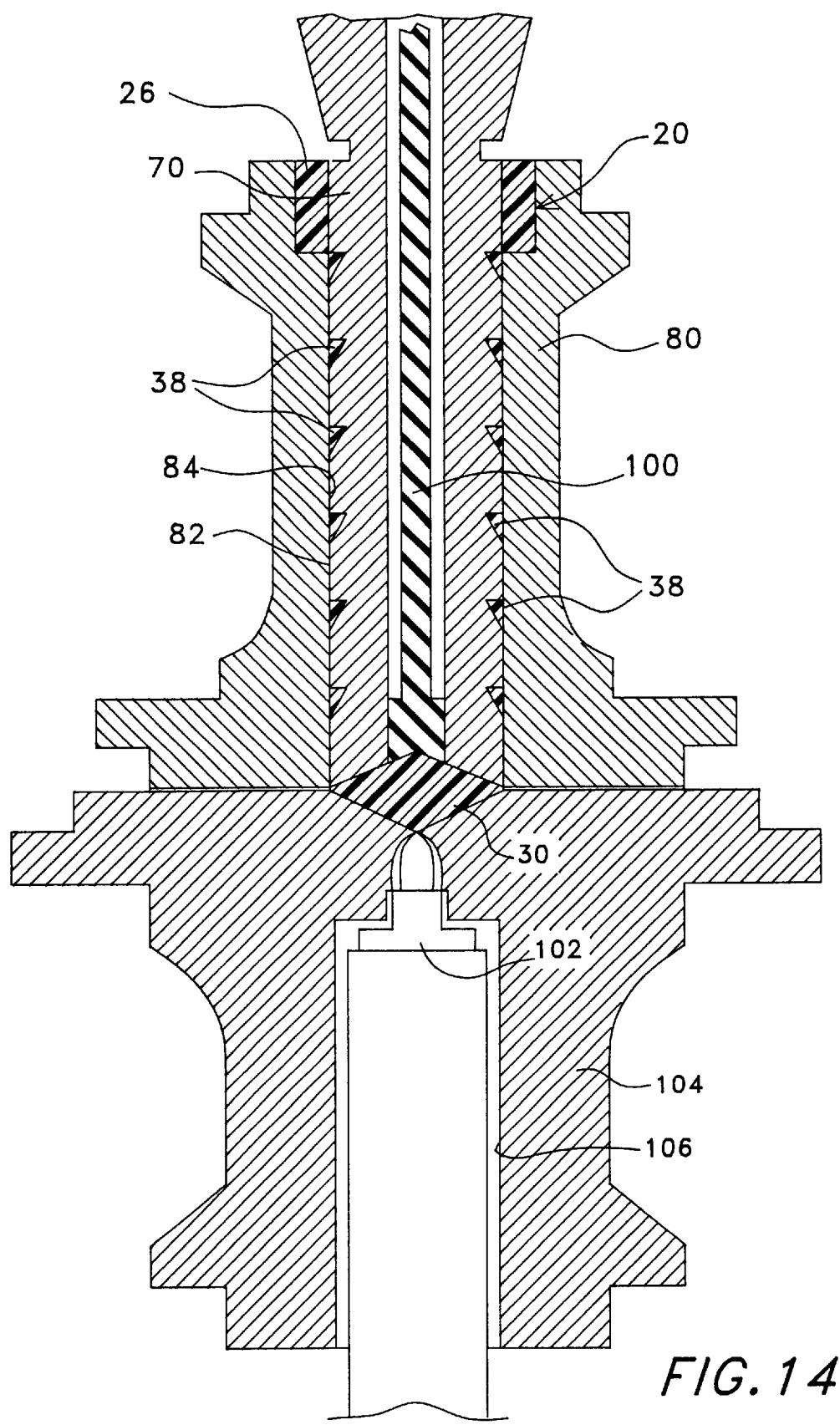
FIG. 14 is a cross sectional view of the core and cavity of FIGS. 12 and 13 in operative molding position relative to each other and an injection nozzle and base.

Referring now specifically to FIG. 14, this shows the closed position in which the core 70 is disposed inside the cavity 80 for the actual molding of a filter 20. Note, flange 26, several cross portions 38 and the header 30 of a filter 20 are the only visible portions of filter 20 in this cross section. Note also the abutment of the exterior faces 84 of core 70 with the interior face 82 of cavity 80.

There are two additional, functional components shown in FIG. 14; namely a knockout pin 100 disposed inside core 70 and an injection nozzle 102 which is shown disposed inside a nozzle bushing 104. With these parts in place as shown, the mold is complete and raw molten material; typically HDPE, can then be injected through nozzle 102 into the voids left between the mold components shown to thereby complete the molding of the filter 20.

Next, however, the filter must be removed from the mold. First, as the molten filter material begins to cool (cavity 80 can provide some preliminary cooling), core 70 is removed from cavity 80 with the filter 20 remaining on core 70. Knockout pin 100 is carried simultaneously with the core 70 and filter 20 up and out of the cavity 80 during this removal step. Air may be forced up through the nozzle bore 106 into the cavity 80 against the header 30 to assist in this removal. Then, after core removal is complete, knockout pin 100 is forced through core 70 in the relative downward direction of FIG. 14, while core 70 remains stationary or continues on a relative upward track. This movement forces header 30 to move down and away from core 70 carrying the remaining integral parts of filter 20 with it off core 70. It must here be noted that if a substantially cylindrical or only slightly tapered design is desired as is described here, then the choice of material used will be important as well. Specifically, a resilient (deformable, yet shape-retaining) material would be necessary to achieve the removal of filter 20 from the core 70 shown and described here, because the cross members 38, molded as shown, would need to deform outwardly from their respective notched voids in order to slide down and over the corresponding exterior faces 84 of core 70.

Air may be forced downward between the core 70 and the filter 20 to assist in this deformation for removal step. An exaggerated schematic illustrating this principle of deformation with the air assist is shown in FIG. 15. In particular, air would be forced into the circumferential space between the filter flange 26 and the core 70 as shown in FIG. 15. Then, the knockout pin (not shown in FIG. 15) can deliver its downward force and easily push the filter 20 off the core 70. A filter 20 would not generally be expected to deform to the exaggerated extent shown in FIG. 15. Note, the header 30 is shown stretched in FIG. 15 to better illuminate the overall deformation and resilience of a preferred filter 20.

An alternative core shape is shown in FIG. 16 and is introduced at this point to illustrate a manufacturing difficulty inherent therewith. A core 70A as shown in FIG. 16 has special notches 74A which would create the cross portions 38A shown in FIG. 1 6A. Cross portions 38A present a nearly ideal shape because of the top and bottom declining surfaces 40A and 42A, respectively, which together would present very little inlet flow resistance. However, as shown in FIG. 16 during the manufacturing process, the introduction of air along the exterior surface of core 70A into what would be the corresponding space between the core 70A and the filter 20A would not necessarily be sufficient to dislodge the corresponding cross portions 38A from their respective notched voids because of the mold undercut portions numbered 75A in FIG. 16. This makes molding this alternative embodiment difficult. The difficulties presented by mold undercuts in obstructing ejection are understood in the art. Nevertheless, the filter 20A embodiment is an effective alternative for use according to the present invention.

As described above, the preferred method of manufacture involves a two part, core and cavity, mold in which the core is inserted in the cavity to complete the mold. This is contrasted with a three part mold which could implement a core that is enclosable within a two part cavity. The two part cavity would come together about the core from lateral directions. Thus, molds of this are commonly known as side-slide molds. Use of a side-slide mold would present numerous distinct disadvantages here. First, a side-slide mold has the inherent disadvantage of the creation of flashing along the meeting edges of the two cavity parts. This flashing is extra molding material (HDPE, for instance) which would adhere to the outside of the finished product after the molding process. Large amounts of flashing would require an extra processing step for removing this material. Moreover, even if there is a minimal amount of flashing such that removal would be difficult or ineffective, the flashing will nevertheless, present an unsmooth exterior surface for the filter which minimally presents an increased flow resistance which maximally presents a risk of blood clotting leading to the dangers addressed in the background section above. The single mold cavity described above allows for a diamond polished interior surface that yields an extremely smooth end product with no flashing.

Moreover, the side-slide molding process traditionally involves a smooth core with mold voids created by notches formed on the interior surfaces of the two part cavities. Thus, a traditional side-slide mold formed to create the interior descending angled face 38 of the filter 20 described herein would create an undercut mold feature which would make removal of the filter from the cavity very difficult. Indeed, the usual process for product removal in a side-slide is to first open the two cavity parts leaving the product on the core. However, with interior declining faces, lateral movement of the side cavity portions after molding would likely tear the product apart. The undercut mold portions would effectively be fingers stuck into the finished filter which would grip the filter thus disallowing a smooth lateral sideward slide. Thus, traditional side-slides involve only vertical, horizontal and exterior angled surfaces such as that shown in Raabe (see FIG. 9, for example). Raabe presents no such side-slide difficulties; however, it therefore has the perpendicular lower entry problem shown in FIG. 9.

Figure 17:
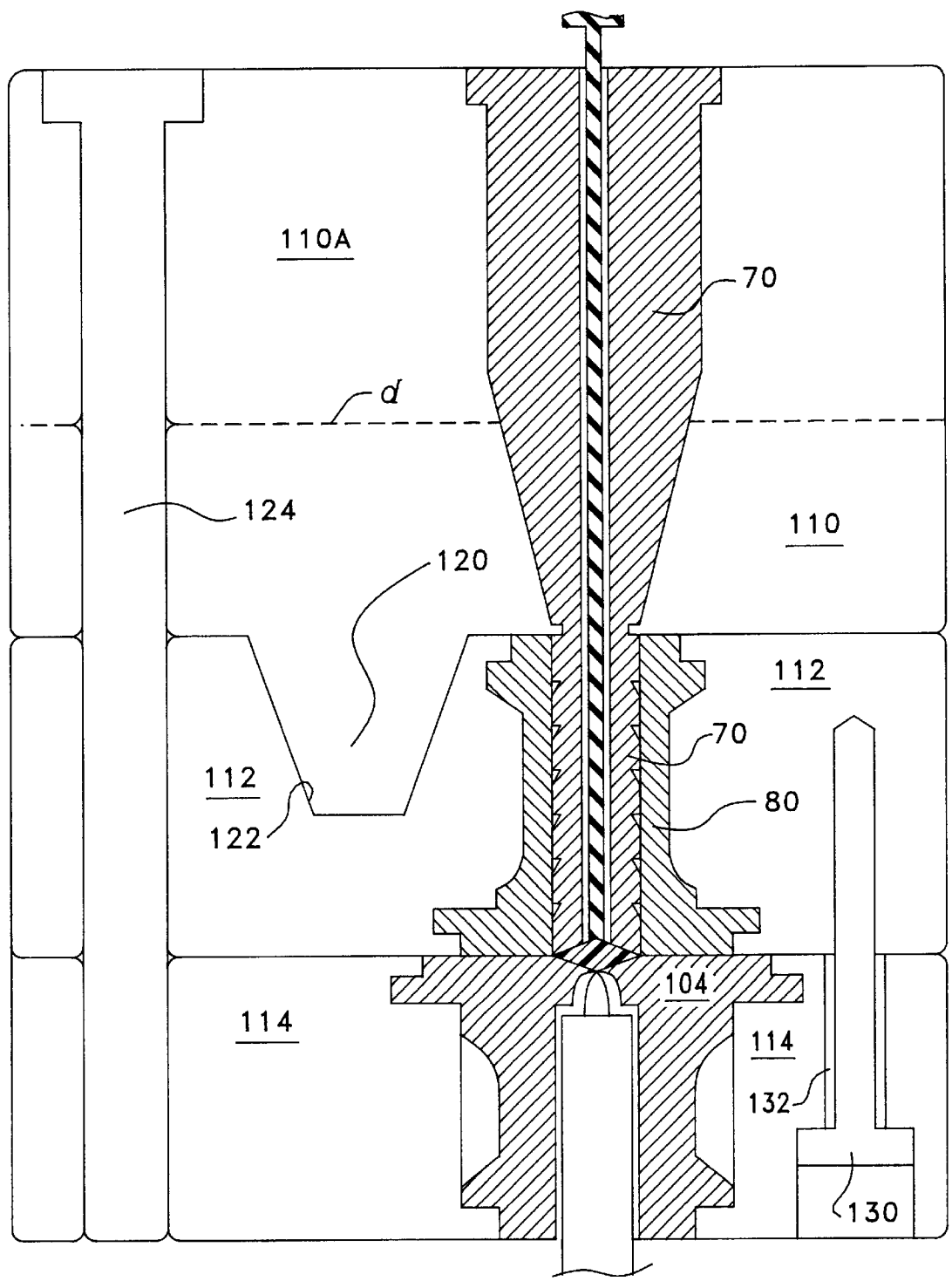
FIG. 17 is a cross-sectional schematic view of the principal elements involved in the injection molding operation of the present invention.
Figure 18:
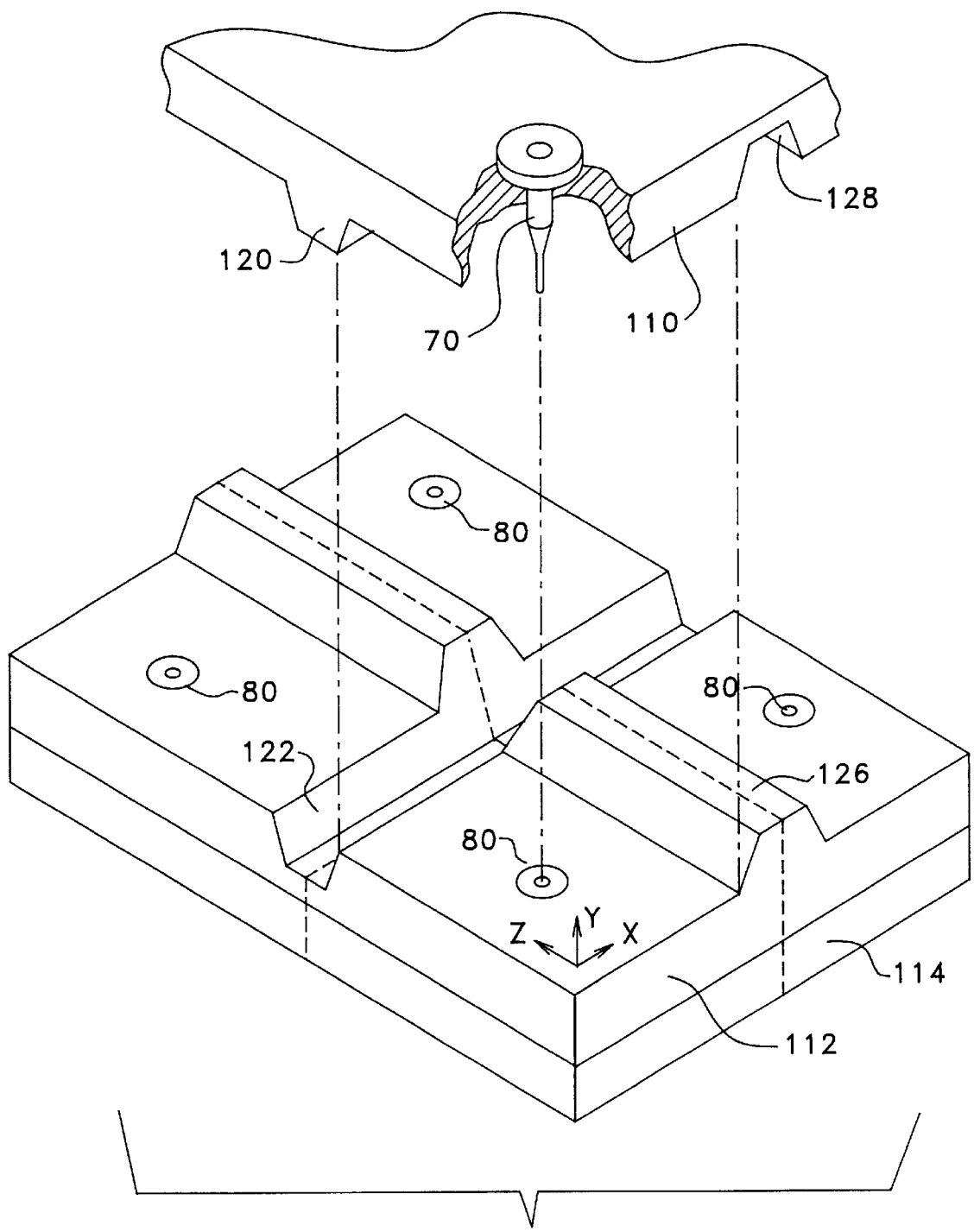
FIG. 18 is a schematic, partially broken-away, isometric view of the molding apparatus of the present invention.

Due also to the extremely close tolerances required by the core and cavity relationship described herein, a further mold alignment approach was developed. In particular and as shown in FIGS. 17 and 18, one or more elongated trapezoidal ridges are formed in the mold base or bases to ensure alignment of the core and cavity. More specifically, and as shown in FIG. 17, a core 70 is disposed inside a cavity 80 in the same fashion shown and described in FIG. 14. However, the respective mold plates which house the core 70 and cavity 80 are also partially shown. Thus, a core plate 110 which houses core 70 is shown in cross section, as is a cavity plate 112, which houses cavity 80. A base plate 114 housing the nozzle bushing 104 is also shown. A male trapezoidal guide 120 is shown as an integral part of plate 110 as it has mated with the female trapezoidal guide 122. As is understood in the art, plates 112 and 114 are stationary (at least in the vertical direction relative to FIG. 17), and plate 110 moves up and down carrying core 70 and knockout pin 100 with it during repetitive filter molding operations. Trapezoidal guides 120 and 122 are used to ensure that as core plate 110 reaches its downward limit (with core 70 inserted in cavity 80), the cavity plate 112 and cavity 80 are fully and exactly aligned with core 70 so that no physically damaging movement will result.

More specifically, the mold portion of core 70 is preferably a fairly small member which must, during routine molding operations, be extensively reciprocated in and out of its corresponding cavity 80, always re-achieving a wall to wall contact relationship with cavity 80 (with the exterior faces 84 of core 70 in full contact with the interior surface 82 of cavity 80). Thus, a high degree of physical stress can be imparted upon the core 70 by even the slightest degree of offset of cavity 80 relative thereto. And, it is understood that in reciprocating injection molding apparatuses of the type described thusfar herein, one portion of the mold will over time and usage, move. This may be due to expansion caused by changes in temperature, or by other effects (the forces of injection will also impart deleterious stresses, both longitudinally and laterally). Usually, it will be the stationary mold plate, such as the cavity plate 112, here, which will accumulate the higher degree of temperature change and thus expansion and relative movement. Therefore, something other than the core 70 would need to move the cavity plate 112 and cavity 80 back into proper molding position, and, a guide pin 124, as is known in the art, will be used herewith for this purpose; however, guide pins, by themselves are not sufficient to absorb the entirety of the expansion and other forces inherent over the width and length of the cavity plate. Therefore, the combination of elongated longitudinal and latitudinal trapezoidal guide members (see FIG. 18, as described below) is thought to provide greater two-dimensional lateral alignment.

Thus, as shown in FIG. 17, a male trapezoidal guide 120 interlocked with a female trapezoidal guide 122 will serve to absorb the largest share of any lateral expansion (or other forces) throughout the respective plates 110 and 112. Moreover, if made sufficiently deep, that is, extending downward longer than core 70 (not shown in FIG. 17), then, the interlocking trapezoidal guide system could be used to perform the pre-alignment function that pin 124 (for example) provides. In this way, a male trapezoidal guide which is longer than a core 70 would, as core plate 110 moves downward, then engage a female guide in cavity plate 112 and thereby force cavity plate 112 into a properly aligned position relative to core plate 110, prior to the ingress of core 70 into cavity 80. Similarly, plate 110 could be broken into two parts along the dashed line l in FIG. 17, such that the first part 110 could be made to come down and force the interlocking mate relationship of guides 120 and 122 prior to the downward movement of core 70 with the second part 110A of the core plate. This way, the alignment will be established prior to ingress of core 70 into cavity 80.

Further, it is often desirable to mold a plurality of filters simultaneously. A system for molding four such filters simultaneously is shown schematically in FIG. 18. There, a cavity plate 112 is shown with four substantially identical cavities 80 and a female trapezoidal guide 122 as described above. A further male trapezoidal guide is shown formed on this cavity plate 112. The alternation of male and female guides on the same plate is primarily for tool manufacturing preference. It does not alter the operation as described. Rather, two female guides could be formed in one plate, as could two male guides formed in another plate; however, the formation of two male guides on one plate is problematic from a metallic tool shaping standpoint. Note, the trapezoidal guides are preferably formed between the respective cavities and cores to enhance the stress distribution along the lengths and widths of the respective plates as described above.

The purpose, again, for these trapezoidal guides is to eliminate the effects of any two dimensional, lateral (as opposed to longitudinal) stresses or movements of the cavity or cavities 80 in or with plate 112. Plate 112 is understood in the art to be a non-moving plate; however, it is also known that with continuous use, a non-moving metallic mold plate will heat up and will thus, naturally expand with the change in temperature ($\Delta T$). The trapezoidal guides 120, 122 and 126, 128 are intended to alleviate the stresses and potential movements caused by this heating.

Yet another related approach to curing this and similar alignment issues is to make the vertically immobile cavity plate 112 two dimensionally floatable relative to plate 114. Thus, as set forth in FIG. 18, cavity plate 112 would be movable in the X-Z plane though still not vertically movable in the Y-dimension. Core plate 110 would remain not movable in the X-Z plane, though still vertically movable (in the Y-dimension). Consequently, when core plate 110 would come down for insertion of core(s) 70 into the respective cavity (or cavities) 80, trapezoidal guides 120, 122 and 126, 128 would move the floating plate 112 into place, and ensure core to cavity alignment. Here also, a pre-alignment pin or pins (not shown in FIG. 18) such as pin 124 in FIG. 17, could also be used for pre-alignment, or, interlocking guides 120, 122, and 126, 128 could be used alone so long as they are sufficiently deep to achieve contact prior to core 70 ingress into cavity 80.

One way to achieve the two dimensional floating of cavity plate 112 as just described, is to attach plate 112 to plate 114 using one or more shoulder bolt(s) 130 as shown in FIG. 17. Bolt 130 is shown firmly affixed in plate 112, but disposed in a sleeve 132 in nozzle plate 114. The firm attachment in plate 112 ensures no vertical movement (base 114 is otherwise firmly affixed in space); however, the sleeve 132 provides some controlled lateral play. Thus. if over usage, the cavity plate 112 or cavities 80 move at all, then the lateral play provided by sleeve 132 allows for the trapezoidal guides to move the cavity plate 112 back to its aligned position for proper mating of cavities 80 with cores 70 for molding.

One farther alternative of this floating approach is to sever what was the previously integrated four part cavity plate shown in FIG. 18, into four separate floating plates. This division could be made along the trapezoid centerlines as shown by the dotted lines in FIG. 18. Thus, each cavity 80 in its respective plate portion may float relative to each of the other cavities 80 and their respective plate portions, only to become properly aligned when the core plate 110 comes down to mate therewith. Still the trapezoidal guides 120, 122 and 126, 128 would preferably do the moving to re-align the floating cavity plate portions.

Accordingly, a new and unique invention has been shown and described herein which achieves its purposes in an unexpected fashion. Numerous alternative embodiments readily foreseeable by the skilled artisan, which were not explicitly described herein are considered within the scope of the invention which is limited solely by the claims appended hereto.

Accordingly, what is claimed is:

1. A fluid filter for use in an extracorporeal blood system comprising:
   an elongated, substantially hollow body portion having an open interior region, an exterior surve, a top end, and a bottom end,
   whereby the body portion has an open base at the bottom end and a closed header portion at the top end;
   said body portion having a plurality of apertures formed therein,
   whereby said aperes are defined side to side by elongated ribs in the length of the body portion, and top to bottom by substantially triangular cross portions having at least one angularly declining, interior face, whereby said at least one angularly declining face is a lower face defining the bottom of each aperture, and whereby said at least one angularly declining face angularly declines from the exterior surface of said body portion to the interior region of said body portion.

2. A fluid filter according to claim 1 in which said substantially triangular cross portions are substantially right triangular.

3. A filter according to claim 1 in which the exterior surface of said body portion is substantially smooth.

4. A fluid filter according to claim 1 in which said ribs and said cross portions are integrally formed during a molding process.

5. A fluid filter according to claim 1 in which said elongated ribs have a substantially prismatic wedge shape.

6. A fluid filter according to claim 1 in which said cross portions have a substantially prismatic wedge shape.

7. A fluid filter according to claim 1 in which said elongated ribs have a relatively narrower nose portion and a relatively wider base.

8. A fluid filter according to claim 1 in which said filter is made of injection molded high density polyethylene.

9. A fluid filter according to claim 1 in which said ribs have a substantially isosceles shaped cross-section.

10. A fluid filter according to claim 1 in which said ribs have a substantially convexly-rounded base corresponding to the external shape of the body portion.

11. A fluid filter according to claim 1 in which blood flows through the plurality of apertures having angularly declining, interior faces at an ever downward orientation.

12. A fluid filter for use in an extaorporeal blood system comprising an elongated, substantially hollow body portion having an open interior region, an exterior surface, a top end, and a bottom end, whereby the body portion bas an open base at the bottom end and a closed header portion at the top end;

said body portion having a plurality of apertures formed therein, said apertures being defined side to side by elongated ribs running the length of the body portion, and top to bottom by cross portions presenting top and bottom angularly declining faces, whereby said angularly declining faces angularly decline from the exterior surface of said body portion to the interior region of said body portion.

13. A fluid filter according to claim 12 in which blood flows through the plurality of apertures at an ever downward orientation.

14. A fluid filter according to claim 12 in which the exterior surface of said body portion is substantially smooth.

15. A fluid filter according to claim 12 in which said ribs and said cross portions are integrally formed during a molding process.

16. A fluid filter according to claim 12 in which said elongated ribs have a substantially prismatic wedge shape.

17. A fluid filter according to claim 12 in which said filter is made of injection molded high density polyethylene.

18. A fluid filter according to claim 12 in which said ribs have a substantially isosceles shaped cross-section.

19. A fluid filter for use in an extaorporeal blood system comprising:

an elongated, substantially hollow body portion having an open base at a bottom end and a closed header portion at the top end;

said body portion having a plurality of apertures formed therein, said apertures being defined side to side by elongated ribs running the length of the body portion, and top to bottom by cross portions presenting a top non-inclining face and a bottom angularly declining face, whereby said bottom angularly declining face angularly declines from the exterior of said body portion to me interior of said body portion.

20. A fluid filter according to claim 19 in which blood flows through the plurality of apertures at an ever downward orientation.

21. A fluid filter according to claim 19 in which said ribs and cross portions are integrally formed during a molding process.

\* \* \* \* \*